United States Patent [19]

Shen

[11] Patent Number: 5,369,213
[45] Date of Patent: Nov. 29, 1994

[54] OXIDATIVE COUPLING OF DIAMONDOIDS AND AROMATICS

[75] Inventor: Dong-Ming Shen, Langhorne, Pa.

[73] Assignee: Mobil Oil Corporation, Fairfax, Va.

[21] Appl. No.: 83,850

[22] Filed: Jun. 30, 1993

[51] Int. Cl.$^5$ .................................................. C07C 13/28
[52] U.S. Cl. ........................................ 585/352; 585/375
[58] Field of Search ................................ 585/352, 375

[56] References Cited

U.S. PATENT DOCUMENTS

| | | | |
|---|---|---|---|
| 3,457,318 | 7/1969 | Capaldi et al. | 260/666 |
| 3,560,578 | 2/1971 | Schneider | 260/648 |
| 3,563,919 | 2/1971 | Schneider | 585/352 |
| 4,174,447 | 11/1979 | Fields | 585/352 |
| 5,019,660 | 5/1991 | Chapman et al. | 585/22 |
| 5,053,434 | 10/1991 | Chapman | 521/52 |

OTHER PUBLICATIONS

Fort, Raymond C., *Adamantane, The Chemistry of Diamond Molecules* (1976).
Chem. Listy, 51, 2335, 1957 (Chem. Abs. 52:6213a).
Collect. Czech. Chem Commun. 24, 93, 1959 (Chem. Abst. 53:7045b).
Synthesis, 692, 1972.
J. Labelled Compd. Radiopham 1991, 29(7), 841–6 (Chem. Abst. 115:114119u).

*Primary Examiner*—Asok Pal
*Attorney, Agent, or Firm*—Alexander J. McKillop; Dennis P. Santini; Robert B. Furr, Jr.

[57] ABSTRACT

The present invention provides a method for arylating a diamondoid compound having at least one unsubstituted bridgehead carbon with an aromatic compound having at least one unsubstituted ring-member carbon comprising reacting said diamondoid compound with said aromatic compound in the presence of an olefin and a catalytically effective amount of a Lewis acid.

8 Claims, No Drawings

OXIDATIVE COUPLING OF DIAMONDOIDS AND AROMATICS

FIELD OF THE INVENTION

This invention relates to the functionalization of polycyclic alkanes. More particularly, this invention provides a method for the oxidative coupling of diamondoids and aromatics in the presence of an olefin.

BACKGROUND OF THE INVENTION

Diamondoid compounds can be converted to their aryl-substituted derivatives in two steps by first halogenating the diamondoid compound and then replacing the halogen with an aryl group. The two-step conversion, requiring separation of an intermediate halogenated organic product, is effective on a bench scale, but the expense of halogenation and the necessary intermediate product separation step have proven to be obstacles to commercialization of the process on an industrial scale. Thus it would be desirable to provide a method for converting non-halogenated diamondoid compounds to their arylated derivatives which could readily operate in a single vessel in the absence of halogenated diamondoid feedstock. The term "diamondoid" is used in its usual sense, to designate a family of polycyclic alkanes including adamantane, diamantane, and triamantane, as well as the higher analogs and their substituted derivatives, examples of which include ethyl- and methyl-substituted diamondoids. For a survey of the chemistry of diamondoid molecules, see Fort, Raymond C., *Adamantane, The Chemistry of Diamond Molecules* (1976) as well as U.S. Pat. Nos. 5,019,660 to Chapman and Whitehurst and 5,053,434 to Chapman. Arylated diamondoids are useful as heat transfer fluids, lubricants, traction fluids, and chemical intermediates. Adamantane has been found to be a useful building block in the synthesis of a broad range of organic compounds, as exemplified by the following references.

U.S. Pat. No. 3,457,318 to Capaldi et al. teaches the preparations of polymers of alkenyl adamantanes useful as coatings, electrical appliance housings, and transformer insulation. The process, yielding polymers bonded through the tetrahedral bridgehead carbons, comprises contacting an adamantyl halide in the presence of a suitable catalyst with a material selected from the group consisting of substituted allyl halides and olefins to produce adamantyl dihaloalkanes or adamantyl haloalkanes as an intermediate product. The intermediate product is then dehalogenated or dehydrohalogenated, respectively, to produce the alkenyl adamantane final product.

U.S. Pat. No. 3,560,578 to Schneider teaches the reaction of adamantane or alkyladamantanes with a $C_3$-$C_4$ alkyl chloride or bromide using $AlCl_3$ or $AlBr_3$ as the catalyst. The reference describes polymerization through $C_3$-$C_4$ linkages connecting bridgehead carbon atoms in the starting adamantane hydrocarbon; See column 3, lines 35-55, as well as the structural illustrations in columns 3-5. Coupling adamantane nuclei through $C_3$-$C_4$ linkages is quite different than arylating diamondoid compounds, and the illustration bridging columns 3 and 4 of the Schneider patent clearly shows the production of a halogenated product. The Schneider patent further teaches that primary or secondary alkyl halides are distinctly preferred. Column 5 at lines 12-16.

Landa et al. reported preparation of 1-phenyl adamantane in relatively low yield by heating 1-bromoadamantane with benzene and sodium. Chem. Listy, 51, 2335, 1957 (Chem. Abstract 52:6213a); Collect. Czech. Chem. Commun. 24, 93, 1959 (Chem. Abstract 53:7045b).

Settler et al. improved the yield of the 1-bromoadamantane/benzene reaction by using ferric chloride as the catalyst. Chem. Ber. 92, 1629, 1959.

Newman used 1-bromoadamantane, benzene, t-butyl bromide, and aluminum chloride to prepare 1-phenyl adamantane, 1,3-diphenyl adamantane, 1,3,5-triphenyl adamantane, and 1,3,5,7-tetraphenyl adamantane. Synthesis, 692, 1972.

More recently, Pilgram et al. disclosed the use of 1-acetoxyadamantane in the arylation of diamondoids. Eur. Pat. Appl. EP 358,574 (Chem. Abstract 113:58678v); J. Labelled Compd. Radiopharm 1991, 29(7), 841–6 (Chem. Abstract 115:114119u).

SUMMARY OF THE INVENTION

The present invention provides a method for arylating a diamondoid compound having at least one unsubstituted bridgehead carbon with an aromatic compound having at least one unsubstituted ring-member carbon comprising reacting said diamondoid compound with said aromatic compound in the presence of an olefin and a catalytically effective amount of a Lewis acid.

Catalysts

Catalysts useful in the present invention include solid and liquid Lewis acid catalysts, for example, Lewis acids which are conventionally used for Friedel-Crafts reactions. Useful Lewis acids include $AlCl_3$, $AlBr_3$, $BF_3$, $BCl_3$, $FeCl_3$, $SnCl_4$, $ZnCl_2$, $TiCl_4$, $FeBr_3$, $SnBr_4$, $ZnBr_2$, and $TiBr_4$. $AlCl_3$ is particularly preferred.

Useful liquid acidic catalysts are exemplified by $BF_3$ complexes, as well as by a solution or complex of an aluminum halide, such as the chloride or bromide, which may be neat or which may be dissolved in a suitable solvent such as hexanes. The aluminum halide may be dissolved in a halogenated organic solvent, for example, a methylene halide such as methylene chloride or methylene bromide.

Operating without special precaution to isolate the reaction mixture from adventitious moisture, the catalyst of the invention does not require proton-releasing promoter. Under other conditions, however, where the scale is much larger or adventitious moisture is insufficient, it may be necessary to add a small amount of a promoter. Examples of suitable promoters include water, alcohols, alkyl halides, hydrogen halides, or mixtures of two or more of these promoters.

Conversion Conditions

Process conditions useful in the diamondoid arylation method of the invention are shown below in Table 1.

TABLE 1

| | Conversion Conditions | |
|---|---|---|
| | Broad Range | Preferred Range |
| Temperature, °C. | −30–200 | 0–100 |
| Pressure, psig | 0–1000 | 0–300 |
| Contact Time, hrs. | 0.25–100 | 4–16 |
| Molar Aromatic:Olefin Ratio | 1:1–40:1 | 1:1–20:1 |
| Molar Aromatic:Diamondoid | 1:1–40:1 | 1:1–20:1 |

TABLE 1-continued

| | Conversion Conditions | |
|---|---|---|
| | Broad Range | Preferred Range |
| Ratio | | |

The term aromatic:olefin ratio, as used herein, is defined as the total molar ratio of aromatic compounds to olefin compounds present in the reaction mixture at the initiation of the reaction (if the method is conducted in a batch mode) or in the feedstream to the reactor (if the method is conducted in a continuous mode). Similarly, the term aromatic:diamondoid ratio, as used herein, is defined as the total molar ratio of aromatic compounds to diamondoid compounds present in the reaction mixture at the initiation of the reaction (if batch mode), or in the feedstream to the reactor (if continuous mode).

The diamondoid feedstock useful in the method of the invention may be produced by mixing individual diamondoid components, by blending mixtures of diamondoids, or by fractionating and treating a naturally occurring diamondoid mixture. U.S. Pat. No. 5,120,899 to Chen and Wentzek teaches a particularly preferred method for recovering a diamondoid-containing mixture from a natural gas stream, and is incorporated by reference as if set forth at length herein.

The lubricant base stock of the invention may be used neat or may be blended with a synthetic or petroleum-based lubricant stock. Examples of useful synthetic lubricant blending stocks are taught in U.S. Pat. Nos. 4,943,383 to Avery et al., 4,952,303 to Bortz et al., 4,962,249 to Chen et al., 4,967,029 to Wu, 4,967,032 to Ho et al., 4,990,709 to Wu, 4,990,718 to Pelrine, 4,990,238 to Cruzman et al., 4,992,189 to Chen et al., 4,995,962 to Degnan, Jr., et al., 5,012,020 to Jackson et al., 5,015,795 to Pelrine, 5,068,046 to Blain et al., and 5,095,165 to Hsia Chen. These patents are incorporated herein for teaching synthetic lubricant blending components.

The Added Olefin

The method of the present invention requires the presence of at least one olefin, preferably at least one mole of olefin per mole of aromatic compound reacted. Useful olefins may contain from 2 to 40 or more carbon atoms, although olefins containing from about 3 to about 5 carbon atoms are preferred to simplify product recovery.

Linear and branched olefins are useful in the present invention, and mixtures of olefins and/or alpha-olefins are also useful as in the present invention.

Isoolefins (which are trisubstituted at the double bond) are preferred for use in the method of the invention, and may be used neat or in mixtures. Examples of useful isoolefins include isobutene, isopentene, isohexene, isoheptene, isooctene, isononene, isodecene, isoundecane, isododecene, isotridecene, isotetradecene, isopentadecene, isohexadecene, isoheptadecene, and isooctadecene. Isobutane and isopentane are particularly preferred.

EXAMPLES

Table 2 shows the compositions for four feedstocks used in the following Examples. The Mixture E referred to in Examples 27 and 28 is the adamantanes fraction of Mixture D in Table 2. Yield is defined as follows:

$$\% \text{ yield} = \left( \frac{\text{weight of product}}{\text{theoretical weight based on } n \text{ and } MWt} \right) \times 100\%$$

where n is the average degree of substitution of aryl groups per diamondoid molecule and MWt is the average molecular weight of the starting materials. For mixtures A and D, the average molecular weights were 237 and 207, respectively. The average molecular weight of mixture E was assumed to be approximately equal to the average molecular weight of mixture A. Because n from GC integration alone underestimates the high molecular weight products, the yields calculated by this method can be over 100%, particularly when the degree of substitution is high.

TABLE 2

| | Compositions of Diamondoid Mixtures Used in Alkylation Reactions (%) | | | |
|---|---|---|---|---|
| Compounds* | A Normally liquid Diamondoid Mixture | B Diamantanes + Mixture | C Adamantanes Mixture | D Partially Liquid Diamondoid Mixture |
| adamantane | 1.364 | none | 1.234 | 8.535 |
| 1-methyl adamantane | 5.615 | none | 7.617 | 22.362 |
| 1,3-dimethyl adamantane | 6.070 | none | 10.174 | 16.552 |
| 1,3,5-trimethyl adamantane | 2.438 | none | 4.796 | 4.413 |
| 1,3,5,7-tetraamethyl adamantane | 0.413 | none | 0.713 | 0.428 |
| 2-methyl adamantane | 1.003 | none | 1.754 | 1.201 |
| t-1,4-Dimethyl adamantane | 1.514 | none | 2.980 | 0.803 |
| c-1,4-Dimethyl adamantane | 1.516 | none | 3.459 | 0.762 |
| 1,3,6-Trimethyl adamantane | 1.774 | none | 4.083 | 0.507 |
| 1,2-Dimethyl adamantane | 1.483 | | 3.368 | 0.753 |
| 1r, 3,4t-Trimethyl adamantane | 2.056 | | 4.647 | 0.528 |
| 1r, 3,4c-Trimethyl adamantane | 2.117 | | 4.898 | 0.538 |
| 1,3,5,6-tetramethyl adamantane | 2.044 | | 5.308 | 0.311 |
| 1-ethyl adamantane | 0.630 | | 1.523 | 0.822 |
| 2,6-; 2e,4e-; 2e,4a-diMe Ad | 0.118 | | 0.285 | 0.036 |
| 1,2,3,5-tetramethyl | 0.07 | | 0.17 | |
| 1-ethyl-3-methyl adamantane | 2.16 | | 5.17 | 1.721 |
| 1,2,3-Trimethyl adamantane | 0.34 | | 0.81 | 0.064 |
| 1-ethyl-3,5-dimethyl adamantane | 1.582 | 0.012 | 3.909 | 0.881 |
| 1-ethyl-3,5,7-trimethyl adamantane | 0.424 | | 1.031 | 0.314 |
| 1,2,3,5,7-pentamethyl adamantane | 1.050 | 0.029 | 2.489 | 0.386 |
| Other adamantanes | 14.432 | 6.631 | 23.083 | 4.432 |
| Total adamantanes | 50.213 | 6.672 | 93.501 | 66.349 |
| Diamantane | 3.967 | 5.560 | 1.342 | 7.485 |

TABLE 2-continued

Compositions of Diamondoid Mixtures Used in Allkylation Reactions (%)

| Compounds* | A<br>Normally liquid<br>Diamondoid Mixture | B<br>Diamantanes +<br>Mixture | C<br>Adamantanes<br>Mixture | D<br>Partially Liquid<br>Diamondoid Mixture |
| --- | --- | --- | --- | --- |
| 4-Methyl-diamantane | 5.345 | 8.338 | 1.522 | 6.277 |
| 4,9-Dimethyl-diamantane | 1.710 | 2.784 | 0.400 | 1.210 |
| 1-Methyl-diamantane | 3.343 | 5.664 | 0.624 | 3.275 |
| 2,4-Dimethyl-diamantane | 2.078 | 3.611 | 0.395 | 1.115 |
| 1,4-dimethyl diamantane | 2.563 | 4.509 | 0.406 | 1.24 |
| 1,4,9-trimethyl diamantane | 1.103 | 1.981 | 0.196 | 0.58 |
| 3-methyl diamantane | 2.384 | 4.241 | 0.359 | 0.649 |
| 4,8-Dimethyl diamantane | 1.618 | 2.970 | 0.195 | 0.251 |
| 4-Ethyl-diamantane | 0.584 | 1.206 | 0.043 | 0.124 |
| Other diamantanes | 16.597 | 34.282 | 1.017 | 3.542 |
| Total diamantanes | 41.292 | 75.146 | 6.499 | 25.748 |
| Triamantane | 1.175 | 2.608 | 0.017 | 0.496 |
| 9-methyl triamantane | 1.151 | 2.583 | 0.016 | 0.264 |
| 9,15-dimethyl triamantane | 0.233 | 0.521 | | 0.039 |
| 3-Me & 3,9-diMe triamantanes | 0.696 | 1.560 | | 0.086 |
| 7,9-diMe & 3,9,15-triMe triamantanes | 0.489 | 1.136 | | 0.060 |
| 4-Me & 4,9,15-triMe triamantanes | 0.440 | 0.973 | | 0.044 |
| 4,9- & 6,9-dimethyl triamantanes | 0.184 | 0.419 | | 0.019 |
| 5-methyl triamantane | 0.289 | 0.661 | | 0.015 |
| 5,9-methyl triamantane | 0.180 | 0.395 | | 0.009 |
| 8-Me & 5,9,15-triMe triamantanes | 0.244 | 0.585 | | |
| 9,14-dimethyl triamantanes | 0.144 | 0.238 | | |
| 8,9-dimethyl triamantanes | 0.069 | 0.210 | | |
| 16-methyl-,a diMe-& a triMe- triamantanes | 0.366 | 0.837 | | |
| 2-methyl triamantane | 0.118 | 0.302 | | |
| other triamantanes | 1.857 | 4.402 | | 0.050 |
| Total triamantanes | 7.605 | 17.430 | 0.033 | 1.082 |
| iso-tetramantane + methyl and dimethyl derivatives | 0.119 | 0.283 | | — |
| anti-tetramantane | 0.023 | 0.059 | | — |
| other tetramantanes | 0.139 | 0.410 | | — |
| Total tetramantane | 0.281 | 0.752 | 0.000 | — |

This sample contained 6.821% of lower boiling materials.
*Prefixes a-, e-, c-, and t- refer to axial, equatorial, cis-, and trans- relationship of substituents in the same cyclohexane ring bearing the substituents in the diamondoids.

Example 1

Adamantane was mixed with toluene in the presence of t-butyl alcohol and methanesulfonic acid under reflux. Add 13.62 g (0.100 mole) adamantane and 200 mL toluene into a 500 mL 2-necked round-bottom flask fitted with a Dean-Stark trap having a reflux condenser and a pressure-equalized addition funnel. Methanesulfonic acid, 1.24 g (12.9 mmoles), was added to the flask with magnetic stir. About 2 mL of a total of 14.82 g (0.200) mole) t-butyl alcohol in the funnel were added to the flask. Then, the reaction mixture was heated to reflux. The rest of the alcohol was added to the reaction mixture. The reaction mixture was refluxed for two hours after finishing adding alcohol. About 3.5 mL of water layer was collected in the trap. GC analysis of the reaction mixture at the end of the reaction showed that it contained only adamantane and toluene. No peaks for tolyl adamantanes were found.

Example 2

Adamantane was mixed with toluene in the presence of t-butyl alcohol, aluminum chloride, and methanesulfonic acid under reflux. Add 13.62 g (0.100 mole) adamantane and 100 mL toluene into a 500 mL 2-necked round-bottom flask fitted with a Dean-Stark trap having a reflux condenser and a pressure-equalized addition funnel. About 3 mL of a total of 14.82 g (0.200 mole) t-butyl alcohol in the funnel were added to the flask, followed by 0.18 g aluminum chloride. No visible change was observed except for developing a yellowish color. Methanesulfonic acid, 0.98 g (10.2 mmoles), was added to the flask with magnetic stir. Then, the reaction mixture was heated. No additional change was observed. The rest of the alcohol was added to the reaction mixture, followed by 0.26 g of aluminum chloride. The reaction mixture was refluxed for 18.7 hours. About 3.5 mL of water layer was collected in the trap. GC analysis of the reaction mixture at the end of the reaction showed that it contained mostly adamantane and toluene. Very small peaks for mono-, di-, and tritolyl adamantanes were observed. However, they only accounted for 2.7% of integrated area, compared to 97.3% for recovered adamantane.

Example 3

Example 3 showed the reaction of a diamondoid mixture with toluene using iso-butene and t-butyl alcohol promoted aluminum chloride catalyst.

Add 49.47 g diamondoid mixture D and 400 mL toluene into an 1 L 4-necked round-bottom flask fitted with two reflux condensers, a mechanical stir, and a gas dispersion tube. A small stream of iso-butene was introduced to the flask with mechanical stir. Anhydrous AlCl$_3$ (0.77 g) was added in two batches during the initial 10 minutes of the reaction. This turned the reaction mixture to yellow and slightly warm. t-Butyl alcohol, 0.50 g was added after 0.5 hour of reaction, followed by 1.02 g of AlCl$_3$ in two portions over the next 5 minutes. At about 2 and 2.7 hours into the reaction, two more batches of AlCl$_3$ (1.02 and 1.07 g) were added, making the total 3.88 g. After 2.75 hours, the flow of iso-butene was stopped. The reaction mixture was stirred for additional 1.5 hours before being transferred into a 2 L separatory funnel with hexanes. The organic layer was separated and washed with 300 mL each of 0.5N HCl (2x), saturated EDTA solution, water, and saturated NaCl. It was further dried over anhydrous Na$_2$SO$_4$. Removal of solvent and unreacted toluene gave 140.57 g orange liquid. The GC of the crude product showed that it contained mostly tolyl diamondoids containing one or more tolyl groups. Only a small amount of the material was unreacted diamondoids or toluene dimers. Vacuum distill the crude product using a 12″ Vigreux column and a Normag distilling apparatus till a b.p. of 108° C./0.25 mm-Hg removed 38.49 g lower boiling material. The remaining 102.0 g viscous orange oil was almost pure aryl diamondoids having one or more aryl groups per diamondoids based on GC analysis. The average degree of substitution was 1.8 aryl groups per diamondoids based on FID GC integration alone. That is, differences in response factors were not taken into account. This is also true for other examples to follow. An estimated yield for this reaction was 116%. A fraction of the crude product boiling between 142° C. and 200° C. at 0.3 mm-Hg had a viscosity of 5.47 cS at 100° C. and a VI of −141. The viscosity changed only 2.9% to 5.63 cS after heating at 300° C. under nitrogen for 24 hours.

Example 4

Example 4 showed the reaction of diamondoids with toluene using iso-butene and aluminum chloride. This example showed that adventitious moisture sufficed as the source of promoter for this reaction. It also showed that the difference in temperature was not the cause for the differences between the results of Examples 1 and 3.

Add 34.32 g adamantane and 300 mL toluene into an 1 L 4-necked round-bottom flask fitted with a reflux condenser having a nitrogen bubbler, a mechanical stir, a thermometer, and a gas dispersion tube. The reaction mixture was heated in an oil bath at 80°–85° C. A stream of iso-butene was introduced to the flask with mechanical stir. Anhydrous AlCl$_3$ (1.47 g) was added in three batches during the initial 30 minutes of the reaction. After 40 minutes, iso-butene flow was stopped. Heating was continued for another 20 minutes before the reaction mixture was cooled and worked up per Example 3. The crude product in this case was 96.11 g orange oil. GC analysis of this crude product showed almost no adamantane. Two major isomers of mono-tolyl adamantanes, three major peaks for di-tolyl adamantanes, and four peaks for tri-tolyl adamantanes were observed. There were probably tetra-tolyl adamantanes present in the product which were not eluted from this column under the conditions used. Average degree of substitution or the number of aryl groups per diamondoid molecule was 2.2 based on GC integration alone. An estimated yield for this reaction was 114%.

Example 5

Example 5 showed the reaction of adamantane with toluene using iso-amylene and aluminum chloride.

Add 13.62 g (0.100 mol) adamantane and 100 mL toluene into a 500 mL 4-necked round-bottom flask fitted with a reflux condenser having a nitrogen bubbler, a mechanical stir, a pressure-equalized addition funnel, and a stopper. Anhydrous AlCl$_3$ (0.46 g) was added. The reaction mixture was heated in an oil bath at about 100° C. A solution of 10.52 g (0.150 mol) iso-amylene in 25 mL toluene was added from the funnel to the flask over 15 minutes. The heating was continued for another hour after finishing adding the olefin. Following the standard work-up, the crude product was evaporated on a rotary evaporator to give 26.07 g orange liquid. Its GC analysis showed only very small amounts of unreacted adamantane and other low-boiling material. Aryl adamantanes having one to three tolyl groups per adamantane accounted for 86% of the integrated area in this GC. The average degree of substitution was 1.4 based on integrated areas alone in GC for these three groups of products. An estimated yield for this reaction was 99%.

Example 6

Example 6 compared the result of the reaction of adamantane with toluene using propylene and aluminum chloride.

Add 13.62 g (0.100 mol) adamantane and 90 mL toluene into a 250 mL 2-necked round-bottom flask fitted with a reflux condenser having a nitrogen bubbler and a gas dispersion tube. Anhydrous AlCl$_3$ (0.28 g) was added. A small stream of propylene was introduced into the reaction mixture for 2.2 hours with magnetic stir. After the first hour, another batch of anhydrous AlCl$_3$ (0.23 g) was added. A total of 25.63 g (0.61 mole) propylene was added during this process. After stirring over night, the reaction mixture was worked up as usual. Only 4.54 g of yellow liquid remained after rotary evaporation. Its GC showed only 12.5% mono-tolyl adamantanes by area. Therefore, conversion of adamantane was quite low under these conditions. The main products were propyl toluenes.

Example 7

Example 7 examined the effect of inert solvent on the reaction of adamantane with substantially stoichiometric amount of toluene using iso-butene and aluminum chloride Add 13.62 g (0.100 mol) adamantane, 23.04 g (0.250 mol) toluene, and 100 mL n-hexane into a 250 mL 2-necked round-bottom flask fitted with a reflux condenser having a nitrogen bubbler and a gas dispersion tube. Anhydrous AlCl$_3$ (0.26 g) was added. A small stream of iso-butene was introduced into the reaction mixture for one hour with magnetic stir. After two hours, another batch of anhydrous AlCl$_3$ (0.18 g) was added. After stirring over night, the reaction mixture was worked up as usual. Following usual work-up, 30.34 g mixture of a white solid and liquid was obtained. Filtering separated 4.55 g white solid from 22.64 g colorless liquid. The former was 90% adamantane and some aryl adamantanes. The latter was −2:1:5 mixture of t-butyl toluenes, adamantane, and aryl adamantanes based on GC integration areas. The average degree of substitution for the aryl adamantanes was 1.2. An estimated yield was 58%.

Examples 8 and 9

Examples 8 and 9 examined the arylation of adamantane with t-butyl benzene using aluminum chloride or aluminum bromide without olefin.

Example 8

Add 13.62 g (0.100 mol) adamantane and 65.63 g (0.49 mol) t-butyl benzene into a 500 mL round-bottom flask fitted with a reflux condenser having a nitrogen bubbler. Anhydrous AlCl$_3$ (0.29 g) was added. The reaction mixture was stirred magnetically. After 1.5 hours, a yellow precipitate began to form. Heat the reaction mixture with a 80° C. oil bath for 15 hours after stirring at room temperature for 2.5 hours. Transfer the sticky solid product into a beaker and stir with hot dilute HCl for 3 days. Filter, wash the solid with water, dry to give 44.47 g slightly yellowish solid. Carbon-13 NMR and GC analyses showed that it was mainly a mixture of 1,3,5,7-tetraphenyl adamantane and 1,3,5-triphenyl adamantane. The estimated yield was −100%.

Example 9

Add 6.81 g (0.050 mol) adamantane and 40.27 g (0.30 mol) t-butyl benzene into a 250 mL round-bottom flask fitted with a reflux condenser having a nitrogen bubbler. A solution of $AlBr_3$ in $CH_2Br_2$ (1.0M from Aldrich, 2.5 mL) was added. This turned the clear colorless mixture to red immediately. The reaction mixture was stirred magnetically for 3 hours at room temperature. Heat the reaction mixture with a 90° C. oil bath for 24 hours. The greenish solid and liquid reaction mixture was filtered, washed thoroughly with water, dilute HCl, and hexanes. The crude product was transferred into a beaker and stirred with 400 mL dilute HCl at slightly elevated temperatures. It was then filtered, washed with water, and dried to give 10.57 g yellowish solid. It was not soluble in $CDCl_3$ and its saturated solution in $CDCl_3$ did not show much signal in carbon-13 NMR, indicating that it was a polymeric material.

Examples 10–19

Examples 10–19 showed the reactions of diamondoids mixture A with alkyl benzenes using iso-butene and aluminum chloride. Examples 18 and 19 showed that the recovered diamondoids from these reactions can be further reacted to give aryl diamondoids. Results are summarized in Table 3.

General procedure for Examples 10–19: Add diamondoids mixture A and the alkyl benzene reactants into a 2 or 1 L 4-necked round-bottom flask fitted with a condenser having a $N_2$ bubbler, a thermometer, a gas dispersion tube immersed below the surface of the reactants, and a stopper. The gas dispersion tube was connected to a iso-butene tank via a calibrated mass flow controller and a pressure relief valve set at 14 psi. Bubble the iso-butene into the reaction mixture at a desirable rate with magnetic stir. After 5 minutes, anhydrous $AlCl_3$ was added to the flask. This usually caused a gradual warming of the reaction mixture from room temperature to about 30°–35° C. A dark color developed. After an appropriate amount of time, the addition of iso-butene was terminated. The reaction mixture was stirred for an additional period of time to complete the reaction; sometime, mild heating was applied during this period to speed up the reaction and/or to make better use of the olefin added. Then, the reaction mixture was worked up using the usual aqueous wash procedures. This typically involved transferring the reaction mixture into ice water with hexanes and water; separate the layers; wash the organic layer with water, dilute HCl, dilute NaOH, water, and saturated NaCl. The crude product was then distilled under vacuum to remove unreacted diamondoids and low-boiling side-products to give the aryl diamondoid product.

Example 10

The crude product after removing unreacted toluene was 277.22 g yellow oil. Vacuum fractionation using a 12" Vigreux column and a Normag distilling head removed 63.5 g colorless liquid boiling between 30° C./0.1 mm-Hg and about 90° C./0.03 mm-Hg. This contained unreacted diamondoids and some butyl toluenes and bis(butyl) toluenes based on GC. The material left in the pot was 201.76 g dark and viscous oil. GC analysis of the latter showed that it was a mixture of mono-, di-, tri-, and tetra-aryl diamondoids with an average degree of substitution of 1.7 based integrated areas only. An estimated yield for this reaction was 82%.

Example 11

The crude product after removing unreacted toluene was 243.16 g dark oil. Vacuum fractionation using a 12" Vigreux column and a Normag distilling head removed 76.2 g yellowish liquid boiling between 30° C./0.05 mm-Hg and 100° C./0.05 mm-Hg. This contained unreacted diamondoids. The material left in the pot was 162.9 g dark oil. GC analysis of the latter showed that it was a mixture of mono-, di-, tri-, and tetra-aryl diamondoids with an average degree of substitution of 1.5 aryl group per diamondoid molecule based integrated areas only. An estimated yield for this reaction was 69%.

Example 12

The crude product after removing unreacted ethyl benzene was 298.71 g brown liquid having a strong pink/purple fluorescence. Vacuum fractionation using a 12" Vigreux column and a Normag distilling head removed 137.11 g yellowish liquid boiling up to 112° C./0.20 mm-Hg. This contained unreacted diamondoids, products derived from ethyl benzene and iso-butene, and some mono-aryl diamondoids. The material left in the pot was 154.5 g red viscous oil. GC analysis of the latter showed that it was a mixture of mono-, di-, tri-, and tetra-aryl diamondoids with an average degree of substitution of 1.4 based integrated areas only. An estimated yield for this reaction was 64%.

Example 13

This product was prepared using a commercial mixture of xylenes. The crude product after removing unreacted xylenes was 284.33 g dark oil. Vacuum fractionation using a 12" Vigreux column and a Normag distilling head removed 112.52 g yellowish liquid boiling between 28° C./0.3 mm-Hg and 115° C./0.05 mm-Hg. This contained unreacted diamondoids, products derived from xylenes and iso-butene, and some mono-aryl diamondoids. The material left in the pot was 166.26 g dark viscous oil. GC analysis of the latter showed that it was a mixture of mono-, di-, tri-, and tetra-aryl diamondoids with an average degree of substitution of 1.6 based integrated areas only. An estimated yield for this reaction was 65%.

Example 14

The crude product including most of the unreacted cumene was 601.6 g dark liquid. Vacuum fractionation using a 12" Vigreux column and a Normag distilling head removed 189.74 g colorless liquid boiling between 28° C./2.7 mm-Hg and 55° C./0.40 mm-Hg. This was mostly unreacted cumene. Distillation was continued to remove 184.99 g yellowish liquid boiling between 40° C./0.4 mm-Hg and 118° C./0.07 mm-Hg. This fraction contained unreacted diamondoids, products derived from cumene and iso-butene, and some mono-aryl diamondoids. The material left in the pot was 141.66 g dark viscous oil. GC analysis of the latter showed that it was a mixture of mono-, di-, tri-, and tetra-aryl diamondoids with an average degree of substitution of 1.6 based integrated areas only. An estimated yield for this reaction was 53%.

Example 15

The crude product after removing unreacted o-xylene was 283.90 g dark viscous oil. Vacuum fractionation using a 12" Vigreux column and a Normag distilling head removed 82.96 g yellowish liquid boiling between 30° C./0.4 mm-Hg and 123° C./0.06 mm-Hg. This fraction contained unreacted diamondoids, products derived from o-xylene and iso-butene, and some mono-aryl diamondoids. The material left in the pot was 189.78 g dark viscous oil. GC analysis of the latter showed that it was a mixture of mono-, di-, tri-, and tetra-aryl diamondoids with an average degree of substitution of 1.6 based integrated areas only. An estimated yield for this reaction was 74%.

Example 16

This reaction used two low-boiling fractions containing iso-butyl benzene recovered from Example 21. The crude product including unreacted iso-butyl benzene was 571.3 g yellow oil. Vacuum fractionation using a 12" Vigreux column and a Normag distilling head removed 375.9 g colorless liquid boiling between 30° C./0.35 mm-Hg and 110° C./0.35 mm-Hg. This fraction contained mostly iso-butyl benzene and products derived from iso-butyl benzene and iso-butene, plus small amounts of recovered diamondoids. The next fraction of product was 109.9 g yellow oil, boiling between 110° C./0.30 mm-Hg and 200° C./0.35 mm-Hg. It was mostly mono-aryl diamondoids based on GC, having −1.0 aryl group per diamondoids on average. The material left in the pot was 51.1 g very viscous dark oil. This contained products with two or more aryl groups per diamondoid molecule.

Example 17

This reaction used 100 mL fresh sec-butyl benzene plus the low-boiling fraction recovered from Example 24. The crude product including unreacted sec-butyl benzene was 729.3 g red orange liquid. Vacuum fractionation using a 12" Vigreux column and a Normag distilling removed 455.3 g slightly yellow liquid boiling between 30° C./2 mm-Hg ad 121° C./0.6 mm-Hg. This fraction contained mostly unreacted sec-butyl benzene, its products with iso-butene, and some unreacted diamondoids. The next fraction of product was 148.5 g yellow oil, boiling between 120° C./0.6 mm-Hg and −200° C./0.6 mm-Hg. Its GC showed that it contained mostly mono-aryl diamondoids, on average having −1.0 aryl group per diamondoids. The material left in the pot was 59.8 g very viscous dark oil. This contained products with two or more aryl groups per diamondoid molecule.

Example 18

The source of diamondoids in this run was the low-boiling fractions distilled out in Examples 10 and 11 above, totaling 139.7 g which included some t-butyl toluenes. The crude product after removing unreacted toluene was 279.06 g dark oil. Vacuum fractionation using a 12" Vigreux column and a Normag distilling head removed 149.17 g yellow liquid boiling between 35° C./0.15 mm-Hg and about 115° C./0.05 mm-Hg. This contained unreacted diamondoids, some butyl toluenes and bis(butyl) toluenes, and small amounts of tolyl diamondoids. The material left in the pot was 128.1 g dark and viscous oil. GC analysis of the latter showed that it was a mixture of mono-, di-, tri-, and tetra-aryl diamondoids with an average degree of substitution of 1.4 based integrated areas.

Example 19

The source of diamondoids in this run was the low-boiling fractions distilled out in Examples 12–15 and 18 above, totaling 666.77 g which included some toluene, xylenes, ethyl benzene, cumene, and their t-butyl derivatives. To supplement this reaction mixture, 100 mL each of toluene, o-xylene, mixed xylenes, ethyl benzene, cumene were added also. The crude product after removing most of the unreacted aromatic compounds was a brown oil. Vacuum fractionation using a 12" Vigreux column and a Normag distilling head removed 741.78 g colorless liquid boiling between 28° C./0.15 mm-Hg and about 145° C./0.05 mm-Hg. This contained unreacted diamondoids, some of the aromatic compounds used and their t-butyl derivatives. The material left in the pot was 366.9 g dark oil. GC analysis of the latter showed that it was a mixture of mono-, di-, and triaryl diamondoids with an average degree of substitution of −1.2 based integrated areas.

TABLE 3

| | Oxidative Coupling of Diamondoid Mixture A and Aromatics using isobutene and AlCl$_3$ | | | | | | | |
|---|---|---|---|---|---|---|---|---|
| | Diamondoid Mixture A, | Alkyl Benzene | | AlCl$_3$, | isobutene addition | | after adding olefin | |
| Example | grams | Compound | Liter | gram | mL/min | time, min | time, hrs. | T °C. |
| 10 | 150.33 | toluene | 1.02 | 8.38 | 35 | 55 | 70 | r.t. |
| | | | | | 100 | 460 | | |
| 11 | 150.0 | toluene | 1.00 | 3.98 | 100 | 360 | 15 | r.t. |
| 12 | 150.0 | Et-Ph | 0.50 | 4.07 | 100 | 460 | 15 | r.t. |
| 13 | 150.0 | xylenes | 0.50 | 4.02 | 100 | 430 | 18 | r.t. |
| 14 | 150.0 | cumene | 0.50 | 4.02 | 100 | 330 | 4 | r.t. |
| | | | | | 25 | 780 | 70 | 53 |
| 15 | 150.56 | o-xylene | 0.50 | 6.22 | 100 | 510 | 20 | r.t. |
| 16 | 150.0 | i-Bu-Ph | 0.4* | 5.45 | 100 | 315 | 16 | r.t. |
| 17 | 150.0 | sec-But-Ph | 0.5* | 5.5 | 100 | 150 | 3 | 25–43 |
| | | | | | 32 | 840 | | |
| 18 | 139.7* | toluene | 0.30 | 5.68 | 80 | 960 | 1.5 | 52–53 |
| | | | | | | | 20 | r.t. |
| 19 | 666.77* | mixture* | 0.50 | 20.25 | 100 | 1335 | 21 | 35 |

*See text for details

Examples 20–22

Examples 20–22 showed the reactions of pure adamantane with alkyl benzenes using iso-butene and aluminum chloride. The results of Examples 20–22 are summarized in Table 4.

General procedure for Examples 20–22: Add adamantane and starting alkyl benzene in an 1 L 4-necked round-bottom flask fitted with a condenser having a $N_2$ bubbler, a thermometer, a gas dispersion tube immersed below the surface of the reactants, and a stopper. The gas dispersion tube was connected to a iso-butene tank via a calibrated mass flow controller and a pressure relief valve set at 14 psi. Bubble the iso-butene into the reaction mixture at a desirable rate with magnetic stir. After 5 minutes, anhydrous $AlCl_3$ was added to the flask. This usually caused a gradual warming of the reaction mixture from room temperature to about 30°–35° C. A dark color developed. After an appropriate amount of time, the addition of iso-butene was terminated. The reaction mixture was stirred for an additional period of time to complete the reaction. Then, the reaction mixture was worked up using the usual aqueous wash procedures. This typically involved transferring the reaction mixture into ice water with hexanes and water; separate the layers; wash the organic layer with water, dilute HCl, dilute NaOH, water, and saturated NaCl. The crude product was then distilled under vacuum to remove unreacted adamantane and low-boiling side-products to give aryl adamantanes product. See Table 4.

Example 20

During the work-up, 166.5 g colorless liquid was recovered from a trap on a rotary evaporator. A GC analysis showed this low-boiling fraction to contain mainly cumene with small amounts of adamantane and t-butyl cumenes. The crude product was 291.8 g yellowish liquid. Vacuum fractionation of the crude product using a 12" Vigreux column and a Normag distilling head removed 140.5 g colorless liquid having a small amount of a white solid boiling up to about 130° C./0.9 mm-Hg. This contained mainly t-butyl cumenes and small amounts of adamantane and monoaryl adamantane. The material left in the pot was 140.7 g yellow liquid. GC analysis of the latter showed that it was a mixture of mono-, di-, tri-, and tetra-aryl adamantanes with an average degree of substitution of 1.4 based integrated areas only. An estimated yield was 62%.

Example 21

During the work-up, −200 mL colorless liquid was recovered from a trap on a rotary evaporator. A GC analysis showed this low-boiling fraction to contain mainly iso-butyl benzene with small amounts of adamantane and t-butyl iso-butyl benzenes. The crude product was 345.22 g yellowish liquid. Vacuum fractionation of the crude product using a 12" Vigreux column and a Normag distilling head removed 188.3 g yellowish liquid having a small amount of a white solid boiling between 23° C./0.45 mm-Hg and 130° C./0.65 mm-Hg. This contained mainly iso-butyl benzene and t-butyl iso-butyl benzenes plus small amounts of adamantane and monoaryl adamantanes. The material left in the pot was 147.1 g yellow and viscous liquid. GC analysis of the latter showed that it was a mixture of mono-, di-, tri-, and tetra-aryl adamantanes with an average degree of substitution of 1.7 based integrated areas only. An estimated yield was 74%.

Example 22

The crude product was 536.5 g yellowish liquid, which included unreacted starting materials. Vacuum fractionation of the crude product using a 12" Vigreux column and a Normag distilling head removed 356.6 g colorless liquid boiling between 38° C./0.9 mm-Hg and about 115° C./0.9 mm-Hg. This contained mainly sec-butyl benzene and t-butyl sec-butyl benzenes plus a small amount of adamantane. The material left in the pot was 175.6 g yellow and viscous liquid. GC analysis of the latter showed that it was a mixture of mono-, di-, tri-, and tetra-aryl adamantanes with an average degree of substitution of 1.3 based integrated areas only. An estimated yield was 91%.

TABLE 4

| | Oxidative Coupling of Adamantane and Aromatics Using Isobutene and $AlCl_3$ | | | | | | |
|---|---|---|---|---|---|---|---|
| | Adamantane | Alkyl Benzene | | $AlCl_3$ | isobutene addition | | After Adding Olefin |
| Example | gram | Compound | liter | gram | mL/min | time, min | time, hrs. | T °C. |
| 20 | 102.18 | cumene | 0.400 | 6.95 | 50 | 930 | 9 | r.t. |
| 21 | 75.0 | iso-Bu-Ph | 0.500 | 5.1 | 100 | 460 | 23 | r.t. |
| 22 | 85.0 | sec-Bu-Ph | 0.500 | 7.5 | 100 | 600 | 40 | r.t. |

Examples 23 and 24

Examples 23 and 24 showed the reactions of diamondoids mixture C with alkyl benzenes using iso-butene and aluminum chloride. The results of Examples 23 and 24 are summarized in Table 5.

General procedure for Examples 23 and 24: Add diamondoids mixture C and the alkyl benzene reactants in an 1 L 4-necked round-bottom flask fitted with a condenser having a $N_2$ bubbler, a thermometer, a gas dispersion tube immersed below the surface of the reactants, and a stopper. The gas dispersion tube was connected to a iso-butene tank via a calibrated mass flow controller and a pressure relief valve set at 14 psi. Bubble the iso-butene into the reaction mixture at a desirable rate with magnetic stir. After 5 minutes, anhydrous $AlCl_3$ was added to the flask. This usually caused a gradual warming of the reaction mixture from room temperature to about 30°–35° C. A dark color developed. After an appropriate amount of time, the addition of iso-butene was terminated. The reaction mixture was stirred for an additional period of time to complete the reaction. Then, the reaction mixture was worked up using the usual aqueous wash procedures. This typically involved transferring the reaction mixture into ice water with hexanes and water; separate the layers; wash the organic layer with water, dilute HCl, dilute NaOH, water, and saturated NaCl. The crude product was then distilled under vacuum to remove unreacted diamondoids and low-boiling side-products to give the aryl diamondoid product.

Example 23

The two low-boiling fractions from Example 20, totaling 317 g, were used as the source of cumene with additional 200 mL fresh cumene. During the work up of Example 23, 187.8 g colorless liquid was recovered in the rotary evaporator trap. This contained mainly unreacted cumene. The crude product was 496.7 g yellowish liquid. Vacuum fractionation using a 12" Vigreux column and a Normag distilling head removed 285.7 g yellowish liquid boiling between 55° C./7 mm-Hg and 102° C./0.6 mm-Hg. This contained unreacted diamondoids, and some butyl cumenes. The material left in the pot was −200 g orange oil. GC analysis of the latter showed that it was a mixture of mono-, di-, tri-, and tetra-aryl diamondoids with an average degree of substitution of 1.4 based integrated areas. An estimated yield was 72%.

Example 24

The low boiling fraction from Example 22 (356.6 g) was used as the source of sec-butyl benzene with additional 25 mL fresh sec-butyl benzene. The crude product was 541.6 g yellowish liquid. Vacuum fractionation using a 12" Vigreux column and a Normag distilling head removed 393.6 g colorless liquid boiling up to 110° C./1.0 mm-Hg. This contained mostly sec-butyl benzene, its t-butyl derivatives, and some unreacted diamondoids. Next, a fraction boiling between 120° C./0.05 mm-Hg and 198° C./0.10 mm-Hg was collected as the product. It was 100.3 g yellow oil. Its GC analysis showed that it was a mixture of mono- and di-aryl diamondoids with an average degree of substitution of −1.0 based integrated areas. The material left in the pot was 39.6 g orange oil. This contained products with two or more aryl groups per diamondoid unit.

ent. There were about 25 g products having mono- and bis-adamantyl groups attached to 1,2-diphenyl ethane based on purification of hydrogenated products.

TABLE 6

Oxidative Coupling of Adamantane and Aromatics using Iso-amylene and $AlCl_3$

| Example | Aromatic Compound | $AlCl_3$, grams (at time, hr.) | n-hexane, mL | Reaction time after adding olefin, hr. (temperature, °C.) |
|---|---|---|---|---|
| 25 | diphenyl methane | 0.75 (0), 0.63 (7) | 25 + 20[a] | 21 (r.t.), 27 (≈60) |
| 26 | 1,2-diphenyl ethane | 0.64 (0), 0.83 (7) | 50 + 20[b] | 21 (r.t.), 27 (≈60) |

[a]Additional 30 mL of n-hexane was added after 32 hours to make up for evaporative loss.
[b]A solution of 10 mL i-amylene in 10 mL n-hexane was added after 46 hours.

Examples 27 and 28

Examples 27 and 28 demonstrate the coupling method of the invention using diamondoid Mixture E and aromatics with iso-amylene and $AlCl_3$.

General procedure for Examples 27 and 28: Dissolve 0.200 mol of diphenyl methane or 1,2-diphenyl ethane in 90.0 g diamondoid mixture E in a 500 mL 2-necked round-bottom flask fitted with a reflux condenser having a nitrogen bubbler and a pressure-equalized addition

TABLE 5

Oxidative Coupling of Diamondoid Mixture C and Aromatics Using Iso-butene and $AlCl_3$

| Example | Diamondoid Mixture C, grams | Alkyl Benzene Compound | | $AlCl_3$ gram | isobutene addition | | After Adding Olefin | |
|---|---|---|---|---|---|---|---|---|
| | | Compound | liter | | mL/min | time, min | time, hrs. | T °C. |
| 23 | 155 | cumene | ≈0.5* | 9.0 | 75 | 780 | 9 | r.t. |
| 24 | 125.0 | sec-Bu-Ph | ≈0.5* | 5.43 | 100 | 315 | 2.5 | r.t. |

*See text for details

Examples 25–28

Examples 25–28 illustrated the reactions of aromatic compounds with more than one benzene rings.

General procedure for Examples 25 and 26: Add adamantane (29.97 g, 0.220 mol), 0.100 mole diphenyl methane or 1,2-diphenyl ethane, and some n-hexane into a 500 mL 2-necked round-bottom flask fitted with a reflux condenser having a nitrogen bubbler and a pressure-equalized addition funnel. Add the anhydrous $AlCl_3$ catalyst to the flask with magnetic stir. A solution of 17.54 g iso-amylene (MC/B, 95%) in 20 mL n-hexane was added to the flask with stir over 1.5 hours. Additional catalyst was added later during the reaction. The rest was similar to other examples above except methylene chloride was used as the solvent during work-up. The details are summarized in Table 6.

Example 25

The crude product was 47.89 g mixture of red oil and solid after removing some starting material. GC analysis showed a large peak for adamantane. Unreacted diphenyl methane and its amyl derivatives were also present. There were about 25 g products having mono- and di-adamantyl groups attached to diphenyl methane based on purification of hydrogenated products.

Example 26

The crude product was 50.76 g mixture of red oil and solid after removing some starting material. GC analysis showed a large peak for adamantane. Unreacted 1,2-diphenyl ethane and its amyl derivatives were also presfunnel. Add the anhydrous $AlCl_3$ catalyst to the flask with magnetic stir. Neat iso-amylene (0.450 mol) was added to the flask with stir over 1–1.5 hours. Additional catalyst was added later during the reaction. The rest was similar to other examples above except methylene chloride was used as the solvent during work-up. The details are shown in Table 7.

Example 27

The crude product was 145.5 g dark greenish liquid. GC analysis showed the presence of some mono- and bis-diamondoid diphenyl methane products, unreacted diamondoids, diphenyl methane and its amyl derivatives, and amylene oligomers. There were about 70 g products having mono- and bis-diamondoid groups attached to diphenyl methane based on purification of hydrogenated products.

Example 28

The crude product was 162.21 g dark greenish liquid. GC analysis showed the presence of some mono- and bis-diamondoid 1,2-diphenyl ethane products, unreacted diamondoids, 1,2-diphenyl ethane and its amyl derivatives, and amylene oligomers. There were about 80 g products having mono- and bis-diamondoid groups attached to 1,2-diphenyl ethane based on purification of hydrogenated products.

TABLE 7

Oxidative Coupling of Diamondoid Mixture E and Aromatics using Iso-amylene and $AlCl_3$ TABLE 7-continued

| Example | Aromatic Compound | AlCl$_3$, grams (at time, hr.) | Reaction time after adding olefin, hr. (temperature, °C.) |
|---|---|---|---|
| 27 | diphenyl methane | 1.12 (0), 0.96 (2), 1.03 (20) | 20 (r.t.), 29 (58–60) |
| 28 | 1,2-diphenyl ethane | 1.00 (0), 1.11 (2), 1.08 (20) | 20 (r.t.), 29 (55) | a. Additional 25 g of iso-amylene was added between 41 and 44 hours during the reaction.
b. Additional 25 g of iso-amylene was added between 41 and 45 hours during the reaction.

Changes and modifications in the specifically described embodiments can be carried out without departing from the scope of the invention which is intended to be limited only by the scope of the appended claims.

What is claimed is:

1. A method for arylating a diamondoid compound having at least one unsubstituted bridgehead carbon with an aromatic compound having at least one unsubstituted ring-member carbon comprising reacting said diamondoid compound with said aromatic compound in the presence of an olefin and a catalytically effective amount of a Lewis acid.

2. The method of claim 1 wherein the aromatic:olefin molar ratio as defined herein is from about 1:1 to about 1:20.

3. The method of claim 1 wherein the aromatic:diamondoid molar ratio as defined herein is from about 1:1 to about 20:1.

4. The method of claim 1 wherein said Lewis acid comprises at least one selected from the group consisting of AlCl$_3$, AlBr$_3$, FeCl$_3$, SnCl$_4$, ZnCl$_2$, TiCl$_4$, FeBr$_3$, SnBr$_4$, ZnBr$_2$, and TiBr$_4$.

5. The method of claim 4 wherein said Lewis acid is AlCl$_3$.

6. The method of claim 1 wherein the reaction mixture contains no added hydroxyl-containing catalyst promoter.

7. The method of claim 1 wherein the reaction mixture is free of added water, alcohol, or ether.

8. The method of claim 1 wherein the olefin is isobutene or isoamylene.

* * * * *